United States Patent
Rokkam et al.

(10) Patent No.: US 11,708,311 B2
(45) Date of Patent: Jul. 25, 2023

(54) PROCESS FOR ISOMERIZING ISOBUTANE

(71) Applicant: UOP LLC, Des Plaines, IL (US)

(72) Inventors: Ram Ganesh Rokkam, Visakhapatnam (IN); Cora Wang Ploentham, Elk Grove Village, IL (US); Vaibhav Ramesh Thool, Gurugram (IN)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 17/575,424

(22) Filed: Jan. 13, 2022

(65) Prior Publication Data
US 2023/0183152 A1 Jun. 15, 2023

Related U.S. Application Data

(60) Provisional application No. 63/288,273, filed on Dec. 10, 2021.

(51) Int. Cl.
*C07C 5/27* (2006.01)
(52) U.S. Cl.
CPC .................. *C07C 5/2702* (2013.01)
(58) Field of Classification Search
CPC ........... C07C 9/12; C07C 5/2791; C07C 2/60; C07C 5/2724; C07C 5/277; C07C 5/2781; C07C 5/2786; C07C 9/00; C07C 9/14; C07C 9/16; C07C 9/22; C07C 2527/125; C07C 5/2556; C07C 7/04
See application file for complete search history.

(56) References Cited

U.S. PATENT DOCUMENTS

| | | | |
|---|---|---|---|
| 3,812,199 A * | 5/1974 | Chen et al. | B01J 29/087 208/120.15 |
| 4,039,604 A | 8/1977 | Myers | |
| 4,191,845 A | 3/1980 | Rubin | |
| 5,082,989 A * | 1/1992 | Johnson | C07C 5/2791 585/751 |
| 9,302,958 B2 | 4/2016 | Lapinski | |
| 2019/0023998 A1 | 1/2019 | Sundaram | |
| 2021/0277316 A1 | 9/2021 | Funk | |

OTHER PUBLICATIONS

Comelli et al. Catalysis Letters 45 (1997) 227-231.*
Search Report and Written Opinion for PCT/US2022/081015 dated Apr. 17, 2023.

* cited by examiner

*Primary Examiner* — Sharon Pregler
(74) *Attorney, Agent, or Firm* — Paschall & Associates, LLC; James C. Paschall

(57) ABSTRACT

A process for increase conversion and yield and selectivity to normal paraffins by reducing the hydrogen to hydrocarbon ratio for paraffin feeds with substantial butanes. The process works best with a low concentration of heavies and cyclics in the isomerization feed. High normal ratios of equilibrium, isobutane conversion, normal paraffins yield and selectivities are achieved for naphtha feed at low ratios of hydrogen to hydrocarbons.

20 Claims, No Drawings

PROCESS FOR ISOMERIZING ISOBUTANE

CROSS-REFERENCE TO RELATED APPLICATIONS

This application claims priority from U.S. Provisional Application No. 63/288,273, filed Dec. 10, 2021, which is incorporated herein in its entirety.

FIELD

The field is processes for isomerizing light paraffins to increase the concentration of normal paraffins.

BACKGROUND

Ethylene and propylene are important chemicals for use in the production of other useful materials, such as polyethylene and polypropylene. Polyethylene and polypropylene are two of the most common plastics found in use today and have a wide variety of uses. Uses for ethylene and propylene include the production of vinyl chloride, ethylene oxide, ethylbenzene and alcohol.

The great bulk of the ethylene consumed in the production of the plastics and petrochemicals such as polyethylene is produced by the thermal cracking of higher molecular weight hydrocarbons. Steam is usually mixed with the feed stream to the cracking furnace to reduce the hydrocarbon partial pressure and enhance olefin yield and to reduce the formation and deposition of carbonaceous material in the cracking reactors. The process is therefore often referred to a steam cracking or pyrolysis.

The composition of the feed to the steam cracking reactor affects the product distribution. The propensity of particular hydrocarbons to crack is greater than others. The tendency of the hydrocarbons to crack to ethylene normally ranks in the following order: normal paraffins; iso-paraffins: olefins; naphthenes; and aromatics.

One way to upgrade light naphtha is first to separate the naphtha into a normal paraffin rich stream and a non-normal paraffin rich stream; and subsequently convert a substantial amount of the non-normal paraffin stream in an isomerization reactor in the presence of a catalyst into normal paraffins. Isomerization can produce normal butanes with the other normal paraffins as well as isobutane. Separating isoparaffins intended for further isomerization from normal paraffins intended for steam cracking requires a series of fractionation columns and can substantially increase capital cost. Isomerization of isobutane to normal butane is important for making the isomerization process efficient.

An efficient process for separating and converting the isobutanes in light naphtha to normal butane would significantly increase the profitability of steam cracking operations by increasing the yield of high value ethylene and propylene.

BRIEF SUMMARY

We have discovered that isobutane converts to normal butane with higher conversion and selectivity to normal paraffins at lower ratios of hydrogen to hydrocarbon. This is especially true when heavier paraffins including cyclics are largely absent or removed from the butane stream prior to isomerization.

Additional details and embodiments of the invention will become apparent from the following detailed description of the invention.

Definitions

The term "communication" means that fluid flow is operatively permitted between enumerated components, which may be characterized as "fluid communication".

The term "downstream communication" means that at least a portion of fluid flowing to the subject in downstream communication may operatively flow from the object with which it fluidly communicates.

The term "upstream communication" means that at least a portion of the fluid flowing from the subject in upstream communication may operatively flow to the object with which it fluidly communicates.

The term "direct communication" means that fluid flow from the upstream component enters the downstream component without passing through any other intervening vessel.

The term "bypass" means that the object is out of downstream communication with a bypassing subject at least to the extent of bypassing.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottoms stream back to the bottom of the column. Feeds to the columns may be preheated. The top pressure is the pressure of the overhead vapor at the vapor outlet of the column. The bottom temperature is the liquid bottom outlet temperature. Overhead lines and bottoms lines refer to the net lines from the column downstream of any reflux or reboil to the column. Stripper columns may omit a reboiler at a bottom of the column and instead provide heating requirements and separation impetus from a fluidized inert media such as steam. Stripping columns typically feed a top tray and take main product from the bottom.

As used herein, the term "a component-rich stream" or "a stream rich in a component" means that the rich stream coming out of a vessel has a greater concentration of the component than any other stream from the vessel.

As used herein, the term "a component-lean stream" or "a stream lean in a component" means that the lean stream coming out of a vessel has a smaller concentration of the component than any other stream from the vessel.

The term "Cx" is to be understood to refer to molecules having the number of carbon atoms represented by the subscript "x". Similarly, the term "Cx−" refers to molecules that contain less than or equal to x and preferably x and less carbon atoms. The term "Cx+" refers to molecules with more than or equal to x and preferably x and more carbon atoms.

As used herein, the term "separator" means a vessel which has an inlet and at least an overhead vapor outlet and a bottoms liquid outlet and may also have an aqueous stream outlet from a boot. A flash drum is a type of separator which may be in downstream communication with a separator that may be operated at higher pressure.

As used herein, the term "predominant" or "predominate" means greater than 50%, suitably greater than 75% and preferably greater than 90% on the applicable basis in the context.

As used herein, the term "T5" or "T95" means the temperature at which 5 mass percent or 95 mass percent, as the case may be, respectively, of the sample boils using ASTM D-86 or TBP.

As used herein, the term "initial boiling point" (IBP) means the temperature at which the sample begins to boil using ASTM D-7169, ASTM D-86 or TBP, as the case may be.

As used herein, the term "end point" (EP) means the temperature at which the sample has all boiled off using ASTM D-7169, ASTM D-86 or TBP, as the case may be.

DETAILED DESCRIPTION

Isobutanes may be converted to normal butane to supply a valuable feed for a stream cracker. Isobutanes are typically present be in a naphtha feed. In a process to increase the concentration of normal paraffins in a feed stream, C5+ isoparaffins may be isomerized to C5+ normal paraffins. However, we have found that isomerization of C5+ paraffins generates isobutanes. Furthermore, we found that isobutanes mixed with pentanes and heavier hydrocarbons in an isomerization reactor exhibit low conversion and do not reach the applicable normal-C4/C4 equilibrium ratio because the presence of heavies and aromatic rings in the paraffin feed and high hydrogen partial pressure inhibit isobutane conversion.

With these findings we propose to isomerize a butane stream, perhaps a concentrated isobutane stream, with a low ratio of hydrogen to hydrocarbon at the reactor outlet. We have found that this results in greater conversion of isobutane and yield and selectivity to normal paraffins as well as normal butane equilibrium close to 100%. If a paraffin stream charged to an isomerization reactor comprises substantial C5+ hydrocarbons, consideration should be given to separating the C5+ hydrocarbons and feeding the butane stream to an isomerization reactor that is dedicated to isobutane isomerization. The C5+ hydrocarbons can be isomerized in a separate dedicated isomerization reactor.

A butane stream that is suitable for the disclosed process may comprise a hydrocarbon stream predominant in paraffins and comprising at least 5 mol % butanes, suitably at least 25 mol % butanes and preferably predominant in butanes. The butanes in the butane stream may comprise predominantly isobutane. The butane stream may comprise less than 20 mol % pentanes, suitably less than 10 mol % pentanes and preferably less than 5 mol % pentanes. The butane stream may comprise less than 20 mol % C5+ hydrocarbons, suitably less than 10 mol % C5+ hydrocarbons and preferably less than 5 mol % C5+ hydrocarbons. Accordingly, the butane stream may comprise less than 20 mol % cyclic hydrocarbons, suitably less than 10 mol % cyclic hydrocarbons and preferably less than 5 mol % cyclic hydrocarbons. Suitable butane streams may be provided from a refinery unit such as a hydrotreating unit, a hydrocracking unit or a steam cracking unit.

In the process of this disclosure, a naphtha stream may comprise a hydrotreated light naphtha stream comprising substantially C4 to C6 hydrocarbons having a T90 between about 40° C. and about 90° C. The end point may be taken to minimize the presence of hydrocarbons with more than six carbon atoms in the feed. The naphtha stream may comprise normal paraffins, iso-paraffins, naphthenes, and aromatics. Normal paraffins yield more light olefins in a steam cracking unit. Hence, it is desired to increase the concentration of normal paraffins in the naphtha stream. The first step in the process may be a step of separating the naphtha stream into a normal paraffin-rich stream and a non-normal paraffin-rich stream. An adsorption separation unit may be used to separate normal paraffins from non-normal paraffins. Of course, if the naphtha stream predominantly comprises isobutanes with insubstantial concentration of normal butanes, this separation step may be bypassed.

Normal paraffins in the naphtha stream selectively enter or occlude into the porous structure of adsorbent components but branched or cyclic non-normal chain paraffins do not typically enter the pores. The non-normal paraffins exit the process as a raffinate stream. In an aspect, the normal butanes enter or occlude into the porous structure of the adsorbent components while the isobutanes do not typically enter the pores. The same dynamic occurs for the C5-C7 paraffins. Desorbent is used to remove the adsorbed normal paraffins from the pores to provide an extract stream that is distilled from the desorbent to provide a normal paraffins stream that can be charged to a steam cracking unit. Raffinate comprising non-normal paraffins and desorbent may be fed to a raffinate column to separate desorbent from a non-normal paraffin stream. In the raffinate column or in a downstream column, C5+ hydrocarbons can be separated from the non-normal paraffin stream to provide the butane stream and a C5+ hydrocarbon stream.

Normal nonane or normal decane or an even heavier normal paraffin can suitably be used as a desorbent, and 5A molecular sieves produced and sold by UOP LLC in Des Plaines, Ill. may be a suitable adsorbent. The raffinate column 24 may operate in a bottoms temperature range of about 250 to about 290° C. and an overhead pressure of about 450 to about 550 kPa (gauge).

The butane stream may be charged with hydrogen to an isomerization reactor to convert the iso-paraffins to normal paraffins over an isomerization catalyst. Isobutanes may convert to ethane, propane and normal butane. Reactions that promote the production of normal paraffins are iso-paraffin disproportionation reactions, reverse isomerization of iso-paraffins, and paraffin hydrocracking reactions. Cracking of some of the butanes can occur in the first reactor to produce propane and ethane. It is believed that the paraffin disproportionation reactions occur by the combination of two iso-paraffins followed by scission into one lighter paraffin and one heavier paraffin. For example, two isobutanes can combine and form an isopentane and a propane in the presence of hydrogen. The isopentanes can further crack to form a propane and an ethane. A portion of the isobutanes also convert to normal butanes via isomerization reactions. Production of propane and ethane via disproportionation, cracking and isomerization reactions occurs with low production of low-value undesired methane as a cracked product. Thus, there is an increase in the overall yield of the normal paraffins in the isomerization reactor.

The isomerization catalyst may include chlorided alumina, sulfated zirconia, tungstated zirconia or zeolite-containing isomerization catalysts. The high isomerization catalyst may be amorphous, e.g., based upon amorphous alumina, or zeolitic. A zeolitic catalyst would still normally contain an amorphous binder. The catalyst may comprise a sulfated zirconia and platinum as described in U.S. Pat. No. 5,036,035 and EP 0666109 A1 or a platinum group metal on chlorided alumina as described in U.S. Pat. Nos. 5,705,730 and 6,214,764. Another suitable catalyst is described in U.S. Pat. No. 5,922,639. U.S. Pat. No. 6,818,589 discloses a catalyst comprising a tungstated support of an oxide or hydroxide of a Group IVB (IUPAC 4) metal, preferably zirconium oxide or hydroxide, at least a first component which is a lanthanide element and/or yttrium component, and at least a second component being a platinum-group metal component. An advantage of a non-chlorided catalyst, such as a sulfated zirconia catalyst, is the absence of chloride omitting further treatment of the effluent streams from the isomerization reactor. If chlorided alumina catalyst is used as the isomerization catalyst, a chloriding agent should be added to the butane stream.

The isomerization reaction conditions include an average reactor temperature usually ranging from about 40° C. to about 250° C. and preferably about 185° C. to about 240° C. Isomerization reactor operating pressures generally range from pressure of about 690 kPa (g) (100 psig) to about 4.2 MPa (g) (600 psig) and preferably at least 2.1 MPa (g) (300 psig). Isomerization is conducted in the gas phase. Liquid hourly space velocities (LHSV) range from about 1 to about 10 volumes and preferably about 2 to about 6 volumes of hydrocarbon feed per hour per volume of catalyst. Weight hourly space velocities (WHSV) may range from 0.5 to about 5 kg of hydrocarbon feed per kg of catalyst Isomerization of the butane feed stream increases the concentration of normal butanes in the reactor product relative to the butane stream.

We have found that hydrogen partial pressure should be reduced to increase conversion of isobutane and yield and selectivity to lighter normal paraffins. Hydrogen is admixed with the butane stream charged to the isomerization reactor to provide a mole ratio of hydrogen to hydrocarbon that is no more than 0.5 at the reactor outlet and preferably no more than 0.2 at the reactor outlet. The mole ratio of hydrogen to hydrocarbon may be no less than 0.01 at the reactor outlet. Hydrogen partial pressure should be 35 kPa (g) (5 psig) to about 1 MPa (g) (150 psig) and preferably about 69 kPa (g) (10 psig) to about 344 kPa (g) (50 psig).

We have found that at low hydrogen partial pressure conditions, isobutane conversion can reach 45% and suitably 50%. At low hydrogen partial pressure, selectivity to normal paraffins can reach 45% and suitably 50%.

Selectivities also increased at low ratios of hydrogen to hydrocarbon at the reactor outlet. The ratios of normal paraffins to methane, normal C2-C6/C1, at low ratios of hydrogen to hydrocarbon may be above about 15 and may reach greater than or equal to about 18. Moreover, selectivities to ethane and propane also increased in terms of the ratio of ethane and propane to methane, C2+C3/C1, which may be greater than about 10 at low ratios of hydrogen to hydrocarbon and greater than or equal to about 25 or even about 100. The selectivity to ethane and propane among other light normal paraffins, C2+C3/normal C2-C6, at low ratios of hydrogen to hydrocarbon may be about 0.35 and even greater than about 0.4.

Contacting within the isomerization reactor may be effected using the isomerization catalyst in a fixed-bed system, a moving-bed system, a fluidized-bed system, or in a batch-type operation. The reactants may be contacted with the bed of high isomerization catalyst particles in upward, downward, or radial-flow fashion. If multiple isomerization reactors are employed the isomerization effluent streams should be cooled between reactors because isomerization generate an exotherm across the reactors. Normal butane equilibrium ratio can exceed 85%, suitably 90% and preferably 95%. Normal pentane equilibrium ratio can exceed 98% and preferably 99%. Normal hexane equilibrium ratio can exceed 95% and preferably 96%.

In an embodiment, the stream of C5+ hydrocarbons removed from the paraffin stream may be isomerized in a separate isomerization reactor to increase the concentration of normal paraffins at a hydrogen to hydrocarbon ratio at the reactor outlet and a hydrogen partial pressure one or both greater than those employed for isomerizing the butane stream. The hydrogen to hydrocarbon ratio at the outlet of the separate isomerization reactor should be about 0.3 to about 1.5. The hydrogen partial pressure employed in the separate reactor should be between about 1.0 MPa (150 psia) and about 2.4 MPa (350 psia).

Example

We conducted a series of experiments to determine the impact of hydrogen partial pressure on a butane stream undergoing isomerization. The butane stream was predominantly butane as shown in Table 1 for the two feeds, A and B with C6+ including cyclics removed. Isomerization runs were made with sulfated zirconia catalyst at relatively high hydrogen to hydrocarbon ratio and relative low hydrogen to hydrocarbon ratio to compare performance at 3.4 kPa pressure.

TABLE 1

| Component, wt % | Feed A | Feed B |
|---|---|---|
| $iC_4$ | 88.8 | 88.8 |
| $nC_4$ | 7.7 | 7.7 |
| $iC_5$ | 3.5 | 3.5 |
| $nC_5$ | 0.0 | 0.0 |
| $iC_6$ | 0.0 | 0.0 |
| $nC_6$ | 0.0 | 0.0 |
| Cyclopentane | 0.0 | 0.0 |
| $C_7+$ | 0.0 | 0.0 |
| SUM | 100.0 | 100.0 |
| Normal $C_2 - C_6$ | 7.7 | 7.7 |

Conditions and products are shown in Table 2.

TABLE 2

| | Run | | | |
|---|---|---|---|---|
| | A1 | A2 | B1 | B2 |
| Ave. Bed Temp., ° C. | 207 | 207 | 196 | 197 |
| LHSV, $hr^{-1}$ | 5.9 | 5.9 | 2.94 | 2.94 |
| $H_2$/HCBN outlet | 0.60 | 0.07 | 0.98 | 0.04 |
| $H_2$ partial pressure, kPa | 1.32 | 0.23 | 1.75 | 0.12 |
| $H_2$, wt % | 2.11 | 0.73 | 3.34 | 0.20 |
| $C_1$, wt % | 2.93 | 2.74 | 2.83 | 2.96 |
| $C_2$, wt % | 3.86 | 4.34 | 3.14 | 5.08 |
| $C_3$, wt % | 9.50 | 14.82 | 8.74 | 18.08 |
| $iC_4$, wt % | 50.65 | 40.64 | 55.82 | 38.39 |
| $nC_4$, wt % | 28.58 | 30.31 | 24.34 | 28.68 |
| $iC_5$, wt % | 1.70 | 4.34 | 1.32 | 4.47 |
| $nC_5$, wt % | 0.61 | 1.56 | 0.45 | 1.55 |
| $iC_6$, wt % | 0.05 | 0.45 | 0.03 | 0.52 |
| $nC_6$, wt % | 0.01 | 0.07 | 0.00 | 0.08 |
| Cyclopentane, wt % | 0 | 0 | 0 | 0 |
| $C_7+$, wt % | 0 | 0 | 0 | 0 |
| SUM, wt % | 100 | 100 | 100 | 100 |
| Normal $C_2 - C_6$, wt % | 42.7 | 51.94 | 36.9 | 53.6 |
| Normal $C_2 - C_6/C_1$ | 14.6 | 18.6 | 13.0 | 18.1 |
| $iC_4$ Conversion | 41.5 | 54.1 | 35.0 | 56.4 |
| $C_2 + C_3/C_1$ | 6.3 | 26.4 | 3.6 | 113.5 |
| $C_2 + C_3$/normal $C_2 - C_6$ | 0.31 | 0.37 | 0.32 | 0.43 |
| $nC_4$, % of Equilibrium | 82 | 98 | 71 | 100 |
| $nC_5$, % of Equilibrium | 98 | 99 | 98 | 99 |
| $nC_6$, % of Equilibrium | 95 | 96 | 93 | 96 |

Disproportionation of the iso-C4 and iso-C5s and isomerization of the produced hydrocarbons produced normal paraffins. The total normal paraffin yield and conversion of isobutane was increased by operating at low ratios of hydrogen to hydrocarbon at the reactor outlet such as no more than 0.5. Due to disproportionation and isomerization at low ratios of hydrogen to hydrocarbon at the reactor outlet, the yield of nC5 and iC5 increased.

Selectivities also increased at low ratios of hydrogen to hydrocarbon at the reactor outlet. The ratios of normal paraffins to methane, normal C2-C6/C1, increased at low ratios of hydrogen to hydrocarbon to above about 15 and greater than or equal to about 18. Moreover, selectivities to ethane and propane also increased in terms of the ratio of ethane and propane to methane, C2+C3/C1, which was greater than about 10 at low ratios of hydrogen to hydrocarbon and greater than or equal to about 25 or about 100 for feeds A and B, respectively. The selectivity to ethane and propane among other light normal paraffins, C2+C3/normal C2-C6, also increased at low ratios of hydrogen to hydrocarbon to greater than about 0.35 and even greater than about 0.4.

Specific Embodiments

While the following is described in conjunction with specific embodiments, it will be understood that this description is intended to illustrate and not limit the scope of the preceding description and the appended claims.

A first embodiment of the disclosure is a process for isomerizing isoparaffins to normal paraffins comprising isomerizing a butane stream comprising at least about 5 mol % butanes over an isomerization catalyst at isomerization conditions in the presence of hydrogen to increase the concentration of normal butanes at a hydrogen to hydrocarbon mole ratio at the outlet of no more than about 0.5. An embodiment of the disclosure is one, any or all of prior embodiments in this paragraph up through the first embodiment in this paragraph further comprising isomerizing isoparaffins in the gas phase. An embodiment of the disclosure is one, any or all of prior embodiments in this paragraph up through the first embodiment in this paragraph wherein the butane stream comprises at least 50 mol % butanes. An embodiment of the disclosure is one, any or all of prior embodiments in this paragraph up through the first embodiment in this paragraph wherein the paraffin stream has less than about 20 mol % pentanes. An embodiment of the disclosure is one, any or all of prior embodiments in this paragraph up through the first embodiment in this paragraph further comprising a hydrogen partial pressure of about 7 kPa to about 2.1 MPa (gauge). An embodiment of the disclosure is one, any or all of prior embodiments in this paragraph up through the first embodiment in this paragraph wherein the hydrogen to hydrocarbon mole ratio at the outlet is about 0.01 to about 0.5. An embodiment of the disclosure is one, any or all of prior embodiments in this paragraph up through the first embodiment in this paragraph further comprising an isomerization pressure of about 690 kPa (g) (100 psig) to about 4.2 MPa (g) (600 psig). An embodiment of the disclosure is one, any or all of prior embodiments in this paragraph up through the first embodiment in this paragraph further comprising an isomerization temperature of about 40° C. to about 250° C. An embodiment of the disclosure is one, any or all of prior embodiments in this paragraph up through the first embodiment in this paragraph wherein the paraffin stream comprises less than 5 about mol % cyclic paraffins. An embodiment of the disclosure is one, any or all of prior embodiments in this paragraph up through the first embodiment in this paragraph further comprising a conversion of isobutane of at least about 45%. An embodiment of the disclosure is one, any or all of prior embodiments in this paragraph up through the first embodiment in this paragraph further comprising removing C5+ hydrocarbons from a paraffin stream to provide the butane stream. An embodiment of the disclosure is one, any or all of prior embodiments in this paragraph up through the first embodiment in this paragraph further comprising isomerizing a stream of C5+ hydrocarbons removed from the paraffin stream and further comprising isomerizing the stream of C5+ hydrocarbons. An embodiment of the disclosure is one, any or all of prior embodiments in this paragraph up through the first embodiment in this paragraph further comprising isomerizing the stream of C5+ hydrocarbons at a hydrogen to hydrocarbon ratio at the reactor outlet of about 0.3 to about 1.5 and a hydrogen partial pressure of about 1.0 MPa (150 psia) to about 2.4 MPa (350 psia). An embodiment of the disclosure is one, any or all of prior embodiments in this paragraph up through the first embodiment in this paragraph further comprising a hydrogen to hydrocarbon mole ratio at the outlet of no more than about 0.2.

A second embodiment of the disclosure is a process for isomerizing isoparaffins to normal paraffins comprising isomerizing a butane stream comprising at least about 5 mol % butanes and less than about 20 mol % pentanes over an isomerization catalyst at isomerization conditions in the presence of hydrogen to increase the concentration of normal butanes at a hydrogen to hydrocarbon mole ratio at the outlet of no more than about 0.5. An embodiment of the disclosure is one, any or all of prior embodiments in this paragraph up through the second embodiment in this paragraph wherein the paraffin stream comprises less than about 5 mol % cyclic paraffins. An embodiment of the disclosure is one, any or all of prior embodiments in this paragraph up through the second embodiment in this paragraph further comprising isomerizing isoparaffins in the gas phase. An embodiment of the disclosure is one, any or all of prior embodiments in this paragraph up through the second embodiment in this paragraph further comprising a hydrogen partial pressure of about 7 kPa to about 2.1 MPa (gauge). An embodiment of the disclosure is one, any or all of prior embodiments in this paragraph up through the second embodiment in this paragraph wherein the hydrogen to hydrocarbon mole ratio at the outlet is about 0.01 to about 0.5.

A third embodiment of the disclosure is a process for isomerizing isoparaffins to normal paraffins comprising isomerizing a butane stream comprising at least about 5 mol % butanes and less than about 20 mol % pentanes over an isomerization catalyst at isomerization conditions in the presence of hydrogen to increase the concentration of normal butanes at a hydrogen to hydrocarbon mole ratio at the outlet of about 0.01 to about 0.2.

Without further elaboration, it is believed that using the preceding description that one skilled in the art can utilize the present disclosure to its fullest extent and easily ascertain the essential characteristics of this disclosure, without departing from the spirit and scope thereof, to make various changes and modifications of the disclosure and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for isomerizing isoparaffins to normal paraffins comprising:
 isomerizing a butane stream comprising at least about 5 mol % butanes and in which butanes comprise predominantly isobutane over an isomerization catalyst at isomerization conditions in the presence of hydrogen to increase the concentration of normal butanes at a hydrogen to hydrocarbon mole ratio at the outlet of no more than about 0.5.

2. The process of claim 1 further comprising isomerizing isoparaffins in the gas phase.

3. The process of claim 1 wherein the butane stream comprises at least 50 mol % butanes.

4. The process of claim 1 wherein the paraffin stream has less than about 20 mol % pentanes.

5. The process of claim 1 further comprising a hydrogen partial pressure of about 7 kPa to about 2.1 MPa (gauge).

6. The process of claim 1 wherein the hydrogen to hydrocarbon mole ratio at the outlet is about 0.01 to about 0.5.

7. The process of claim 1 further comprising an isomerization pressure of about 690 kPa (g) (100 psig) to about 4.2 MPa (g) (600 psig).

8. The process of claim 1 further comprising an isomerization temperature of about 40° C. to about 250° C.

9. The process of claim 1 wherein the paraffin stream comprises less than 5 about mol % cyclic paraffins.

10. The process of claim 1 further comprising a conversion of isobutane of at least about 45%.

11. The process of claim 1 further comprising removing C5+ hydrocarbons from a paraffin stream to provide said butane stream.

12. The process of claim 10 further comprising isomerizing a stream of C5+ hydrocarbons removed from the paraffin stream and further comprising isomerizing the stream of C5+ hydrocarbons.

13. The process of claim 8 further comprising isomerizing the stream of C5+ hydrocarbons at a hydrogen to hydrocarbon ratio at the reactor outlet of about 0.3 to about 1.5 and a hydrogen partial pressure of about 1.0 MPa (150 psia) to about 2.4 MPa (350 psia).

14. The process of claim 1 further comprising a hydrogen to hydrocarbon mole ratio at the outlet of no more than about 0.2.

15. A process for isomerizing isoparaffins to normal paraffins comprising:
    isomerizing a butane stream comprising at least about 5 mol % butanes and less than about 20 mol % pentanes and in which butanes comprise predominantly isobutane over an isomerization catalyst at isomerization conditions in the presence of hydrogen to increase the concentration of normal butanes at a hydrogen to hydrocarbon mole ratio at the outlet of no more than about 0.5.

16. The process of claim 15 wherein the paraffin stream comprises less than about 5 mol % cyclic paraffins.

17. The process of claim 15 further comprising isomerizing isoparaffins in the gas phase.

18. The process of claim 15 further comprising a hydrogen partial pressure of about 7 kPa to about 2.1 MPa (gauge).

19. The process of claim 15 wherein the hydrogen to hydrocarbon mole ratio at the outlet is about 0.01 to about 0.5.

20. A process for isomerizing isoparaffins to normal paraffins comprising:
    isomerizing a butane stream comprising at least about 5 mol % butanes and less than about 20 mol % pentanes and in which butanes comprise predominantly isobutane over an isomerization catalyst at isomerization conditions in the presence of hydrogen to increase the concentration of normal butanes at a hydrogen to hydrocarbon mole ratio at the outlet of about 0.01 to about 0.2.

\* \* \* \* \*